United States Patent [19]

Homeier et al.

[11] 4,292,196

[45] Sep. 29, 1981

[54] CATALYST RECOVERY

[75] Inventors: Edwin H. Homeier, Maywood; Alan R. Dodds, Elgin; Tamotsu Imai, Mt. Prospect, all of Ill.

[73] Assignee: UOP Inc., Des Plaines, Ill.

[21] Appl. No.: 101,949

[22] Filed: Dec. 10, 1979

[51] Int. Cl.³ .................. B01J 31/40; C07C 29/16; C07C 45/50; C07C 29/86
[52] U.S. Cl. .................. 252/412; 423/22; 568/451; 568/454; 568/455; 568/909
[58] Field of Search ............ 252/412, 414, 431 M; 423/22; 568/451–456, 909

[56] References Cited

U.S. PATENT DOCUMENTS

| | | | |
|---|---|---|---|
| 2,822,409 | 2/1958 | Gwymm et al. | 568/451 |
| 3,530,190 | 9/1970 | Olivier | 568/455 |
| 3,594,425 | 7/1971 | Brader, Jr. et al. | 568/455 |
| 3,755,393 | 8/1973 | Kniese et al. | 252/412 |
| 3,896,047 | 7/1975 | Aycock et al. | 252/412 |
| 4,096,188 | 6/1978 | Wilkes | 568/451 |

FOREIGN PATENT DOCUMENTS 2311388  9/1974  Fed. Rep. of Germany ...... 252/414

*Primary Examiner*—P. E. Konopka
*Attorney, Agent, or Firm*—James R. Hoatson, Jr.; Raymond H. Nelson; William H. Page II

[57] ABSTRACT

Catalysts which comprise metal carbonyls or organometallic complexes in which the metal portion of the complex is selected from a Group VIII metal are useful in hydroformylation reactions. The catalysts which are homogeneous in nature may be recovered from the hydroformylation products by treating the catalyst complex with a nitrogen-containing compound in an aqueous phase whereby said catalyst may be easily separated from the hydroformylation products and recovered.

8 Claims, 1 Drawing Figure

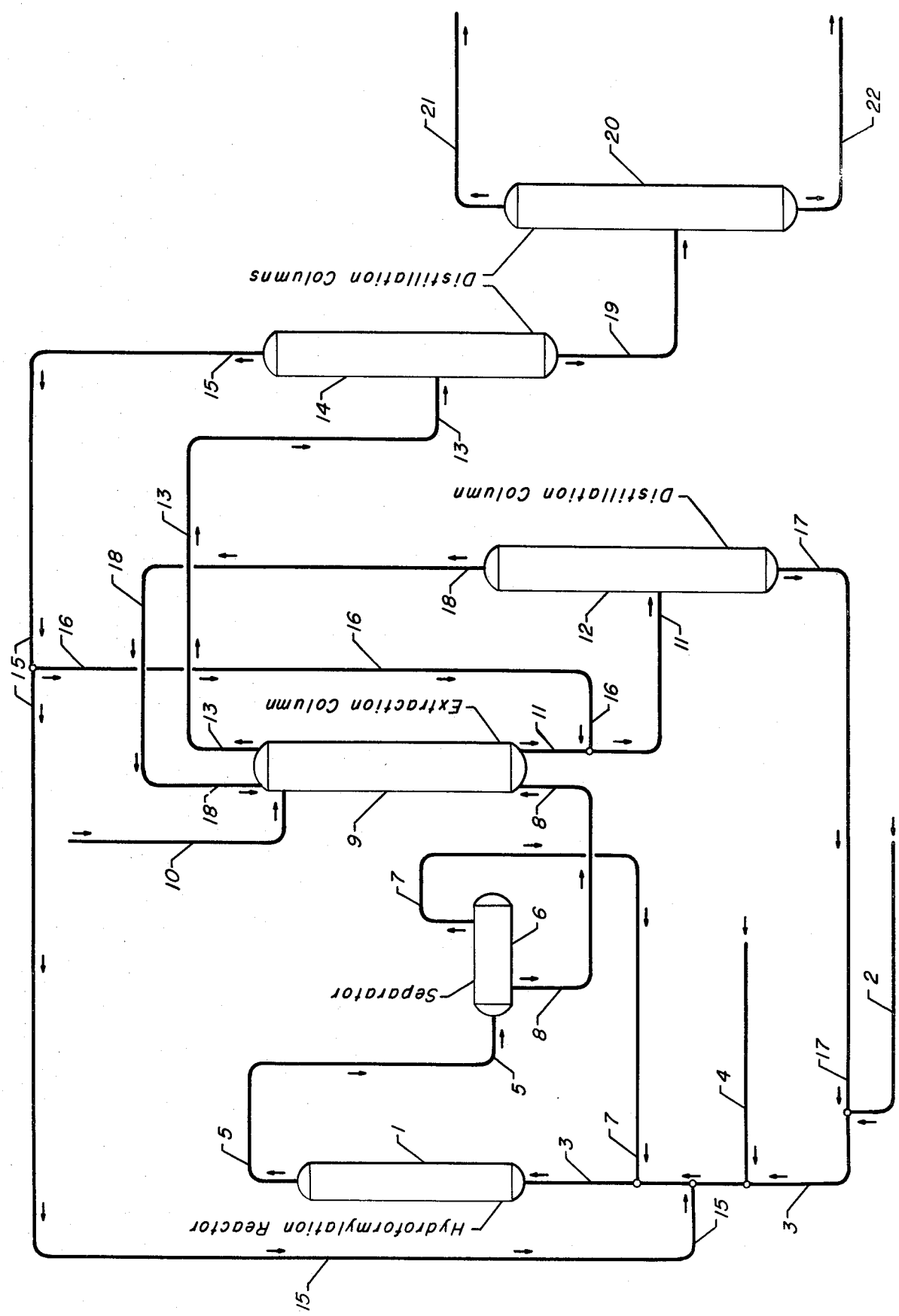

CATALYST RECOVERY

This invention relates to a process for the recovery of catalysts. More specifically, the invention is concerned with a process whereby certain catalytic compositions of matter comprising metal carbonyls or organometallic complexes of the type hereinafter set forth in greater detail which are used in hydroformylation reactions may be separated and recovered from the products of said hydroformylation reaction.

Hydroformylation reactions in which an olefinic compound and particularly an olefinic hydrocarbon is treated with carbon monoxide and hydrogen in the presence of certain catalytic compositions of matter results in the formation of oxygen-containing compounds such as aldehydes and alcohols. The formation of these compounds presents an attractive route due to the fact that olefins or mixtures of olefins which may be formed during other processes, such as certain refinery processes, constitute a relatively inexpensive feed stock which may be used in the formation of the desired products. It is well known in the chemical art that aldehydes and alcohols constitute an important class of compounds. For example, relatively long chain primary alcohols such as n-dodecanol (lauryl alcohol) is an important intermediate in the preparation of synthetic detergents as well as lube additives, pharmaceuticals, rubber, textiles and perfumes. Likewise, n-tetradecanol (myristyl alcohol) is useful intermediate in the preparation of plasticizers as well as being used as an antifoam agent, an intermediate in the preparation of perfume fixitives for soaps and cosmetics, as well as being a base for the manufacture of wetting agents and detergents, while n-hexadecanol (cetyl alcohol) is used as an intermediate for the preparation of compounds useful in medicines, perfumes, emulsifiers, cosmetics, etc. Lower molecular weight alcohols such as butanol is utilized by the preparation of esters such as butyl acetate, as a solvent for resins and coatings, as well as being used in plasticizers, detergent formulations, dehydrating agents, hydraulic fluids, etc. Likewise, aldehydes are useful in the chemical industry. For example heptanal is useful in organic synthesis in the manufacture of rubber products, pharmaceuticals, perfumes, etc.; caprylic aldehyde (octanal) is used in flavors and perfumery; capric aldehyde (n-decanal) is used as a solvent; lauryl aldehyde (dodecanal) is used in perfumery, etc.

The preparation of these oxygen-containing compounds is effected by treating an olefin with carbon monoxide and hydrogen in the presence of a catalyst, preferably a metal carbonyl or an organometallic complex in which the metal portion of the complex is selected from the metals of Group VIII of the Periodic Table, and preferably rhodium. In addition, the reaction is also effected in the presence of a nitrogen-containing compound which acts as a modifier for the catalyst and thus permits a greater recovery of the desired hydroformylation product than would be permitted without the use of said modifier. The particular catalyst complex which is utilized to effect the hydroformylation reaction is homogeneous in nature and therefore must be recovered from the hydroformylation products. Inasmuch as the preferred metal comprises rhodium which is expensive, it is necessary to effect the recovery of the catalyst in such a manner so as to minimize the loss of the catalyst. In this respect, it has now been discovered that by treating the hydroformylation product stream which results from the hydroformylation reaction, and which contains at least a portion of the catalyst, with a nitrogen-containing compound of the type hereinafter set forth in greater detail, it is possible to extract the active metal catalyst from the hydroformylation products and thus permit recovery of said catalyst.

It is therefore an object of this invention to provide a process for the recovery of catalysts.

A further object of this invention is to provide a process for the recovery of hydroformylation catalysts from hydroformylation products utilizing nitrogen-containing compounds to effect said recovery.

In one aspect an embodiment of this invention resides in a process for the extraction of a hydroformylation catalyst comprising a metal carbonyl or an organometallic complex in which the metal is selected from Group VIII of the Periodic Table from the products resulting from a hydroformylation reaction which comprises treating said products with a water-soluble nitrogen-containing compound capable of acting as a complexing agent at reaction conditions, and recovering the resultant metal containing complex.

A specific embodiment of this invention is found in a process for the extraction of a hydroformylation catalyst comprising a metal carbonyl or an organometallic complex in which the metal portion of the complex is rhodium from products resulting from a hydroformylation reaction which comprises treating said products with 2-N,N-dimethylaminoethanol at a temperature in the range of from about ambient to about 100° C. and a pressure in the range of from about 0 to about 1000 psi, and recovering the resultant metal containing complex.

Other objects and embodiments will be found in the following further detailed description of the present invention.

As hereinbefore set forth the present invention is concerned with a process for recovering metal containing catalysts from a hydroformylation reaction which involves the treatment of olefins with carbon monoxide and hydrogen in the presence of these catalysts. The olefins which are subjected to the hydroformylation reaction may be obtained from any source available. For example, the olefins may be recovered from a dehydrogenation reaction of dehydrogenatable hydrocarbons and thus may include a mixture of olefins of various carbon atom lengths. It is also contemplated within the scope of this invention that the olefins which are subjected to the hydroformylation reaction may be obtained from other sources and thus will constitute pure individual olefins. When utilizing dehydrogenatable hydrocarbons as the feed stock, it is preferable to use paraffinic hydrocarbons containing from about 2 to about 30 carbon atoms per molecule such as normal aliphatic hydrocarbons, or cycloaliphatic hydrocarbons containing from about 4 to about 10 carbon atoms. Some specific examples of these suitable dehydrogenatable hydrocarbons will include the aliphatic paraffins such as ethane, propane, the isomeric butanes, pentanes, hexanes, heptanes, octanes, nonanes, decanes, undecanes, dodecanes, tetradecanes, heptadecanes, octadecanes, eicosanes, henicosanes, docosanes, tricosanes, triacontanes, etc.; naphthenes such as cyclobutane, cyclopentane, cyclohexane, methylcyclopentane, cycloheptane, ethylcyclopentane, methylcyclohexane, cyclooctane, 1,3-dimethylcyclohexane, isopropylcyclopentane, etc. While the feed stream of the dehydrogenatable hydrocarbon may comprise one particular paraffinic or cycloparaffinic hydrocarbon, it is also contemplated that the feed stream may contain a mixture of 4 or 5 adjacent normal paraffin homologs such as $C_{10}$–$C_{13}$, $C_{11}$–$C_{14}$, $C_{11}$–$C_{15}$ and the like mixtures.

The products resulting from the aforementioned dehydrogenation reaction or olefins from any other source may then be utilized as feed material for the hydroformylation reaction in which said olefins are contacted or reacted with carbon monoxide and hydrogen in the presence of certain catalytic compositions of matter. The hydroformylation products which are produced by this reaction will comprise oxygenated compounds such as aldehydes or alcohols, the particular product which is obtained being dependent upon reaction conditions employed in the process as well as other factors such as a catalyst modifier which is also present in the reaction mixture. The reaction conditions which are employed for effecting the hydroformylation reaction will include temperatures in the range of from about 50° to about 350° C. and pressures in the range of from about 10 to about 300 atmospheres. In the preferred embodiment of the process the pressures which are employed will be the autogenous pressures resulting from the presence of carbon monoxide and hydrogen in the reaction mixture, although it is also contemplated that the pressures resulting from the use of carbon monoxide and hydrogen will comprise only a partial operating pressure, the remainder of the desired pressure being afforded by the introduction of a substantially inert gas such as nitrogen, helium, argon, etc., into the reaction vessel. Other reaction conditions which are present during the hydroformylation reaction will include mole ratios of the various components. For example, the molar ratio of olefin to the metal portion of the catalyst will be in a range of from about 300:1 to about 3000:1 moles of olefin per mole of metal. Likewise, the molar ratio of catalyst modifier to the metal will be in a range of from about 30:1 to about 300:1 moles of modifier per mole of metal.

Examples of metal carbonyls or organometallic compounds which may be utilized as catalysts for the hydroformylation reaction of the olefin will comprise components in which the metallic portion of the catalyst is selected from the metals of Group VIII of the Periodic Table. Alternatively, the Group VIII metal carbonyl or organometallic complex may be synthesized under hydroformylation conditions from catalyst precursors comprising Group VIII metals, metal salts, metal hydroxides, metal oxides, and metal hydrides, particularly from rhodium, ruthenium, cobalt or iridium containing compounds and, if desired, the synthesis may be performed in situ in the hydroformylation reactor by charging the aforementioned catalyst precursors in the process. Specific examples of these compounds which are employed will include rhodium, rhodium nitrate, rhodium chloride, rohdium bromide, rhodium iodide, rhodium fluoride, chlorodicarbonylrhodium dimer, chlorobis(ethylene)rhodium dimer, hexarhodium-hexadecylcarbonyl, tetrarhodiumdodecylcarbonyl, tris-(acetylacetonato)rhodium(III), rhodium oxide, rhodium oxalate, bis(acetylacetonato)chlororhodiumhydrate, etc., rhthenium, ruthenium nitrate, ruthenium chloride, ruthernium bromide, ruthenium iodide, ruthenium fluoride, ruthenium carbonyl, ruthenium oxide, cobalt, cobalt nitrate, cobalt chloride, cobalt bromide, cobalt oxide, cobalt carbonyl, etc., iridium, iridium nitrate, iridium chloride, iridium bromide, iridium oxide, iridium carbonyl, etc. It is to be understood that the aforementioned metal carbonyls or organometallic complexes are only representative of the class of compounds which may be employed, and that the present invention is not necessarily limited thereto.

In addition to the aforementioned metal carbonyls or organometallic compounds the hydroformylation reaction is also effected in the presence of a nitrogen-containing compound which acts as a modifier or promoter for the catalyst. Examples of nitrogen-containing compounds which may be employed will include ammonia, primary alkyl amines such as methylamine, ethylamine, n-propylamine, isopropylamine, n-butylamine, t-butylamine, aniline, p-tolylamine, cyclopentylamine, cyclohexylamine, etc.; secondary amines such as dimethylamine, diethylamine, di-n-propylamine, diisopropylamine, di-n-butylamine, di-ti-butylamine, dianiline, di-p-tolylamine, dicyclopentylamine, dicyclohexylamine, etc.; tertiary amines such as diemthylpropylamine, dimethylbutylamine, dimethylpentylamine, dimethylhexylamine, dimethylheptylamine, dimethyloctylamine, dimethyldecylamine, dimethyldodecylamine, dimethylpentadecylamine, dimethyleicosylamine, dimethyldocosylamine, diethylpropylamine, diethyloctylamine, diethylundecylamine, dipropylhexylamine, dipropylnonylamine, dipropylheptadecylamine, tributylamine, dibutylpentylamine, dibutyloctylamine, dimethylphenylamine, diethylphenylamine, dipropylphenylamine, dioctylphenylamine, dioctyldecylphenylamine, dipropycyclohexylamine, dihexylcyclohexylamine, didodecylcyclohexylamine, diphenylpropylamine, diphenylhexylamine, diphenylundecylamine, diphenyltetradecylamine, dicyclohexylpropylamine, dicyclohexyloctylamine, di(p-tolyl)octylamine, di(p-tolyl)decylamine, etc.; aromatic amines such as pyridine, triazine, etc., functionalized amines such as 2-aminoethanol, 3-aminopropanol, quinolinesulfonic acid, etc.; amides such as N,N-dimethylformamide, N,N-diethylformamide, N,N-dipropylformamide, N,N-dimethylacetamide, N,N-diethylacetamide, etc.; nitriles such as acetonitrile, propionitrile, butyronitrile, etc. It is to be understood that the aforementioned amines are only representative of the class of compounds which may be employed to modify the aforementioned catalyst.

After effecting the hydroformylation of the olefinic compound, the reaction product is then subjected to further treatment in order to recover the catalyst which may still be present in the reaction mixture. The process of the present invention comprises treating this hydroformylation product mixture with a nitrogen-containing compound whereby the active metal catalyst is extracted from the hydroformylation products and is thus readily recoverable. The nitrogen-containing compounds which are employed to effect this extraction process will comprise those compounds which are water soluble in nature and posses the ability to act as a complexing agent whereby the aforesaid catalyst may be separated or extracted from the hydroformylation products. The nitrogen-containing compound which is utilized for this extraction process may be the same nitrogen-containing compound which was used to modify the catalyst if it possesses the criteria hereinbefore enumerated. Some specific examples of nitrogen-containing compounds which may be utilized for the extraction of the active metal catalyst will include ammonia, ammonium hydroxide, tertiary amines, such as trimethylamine, triethylamine, dimethylethylamine, dimethylpropylamine, diethylpropylamine, etc., alcohol amines such as dimethylethanolamine, diethylethanolamine, dipropylethanolamine, dimethylpropanolamine, diethylpropanolamine, dipropylpropanolamine, etc., polytertiary amines such as N,N,N',N'-tetramethylethylenediamine, N,N,N',N'-tetraethylethylenediamine, N,N,N',N'-tetramethylpropylenediamine, N,N,N',N'-tetraethylpropylenediamine, etc. It is to be understood that the aforementioned nitrogen-containing compounds which may be used to extract the metal are only representative of the class of compounds which may be employed and that the present invention is not necessarily limited thereto.

The hydroformylation reaction reaction of the olefin may be accomplished by utilizing either a batch or continuous type operation. For example, when a batch type of operation is used, a quantity of the olefinic hydrocarbon, a Group VIII metal carbonyl or organometallic complex catalyst and the nitrogen-containing promoter are charged to an appropriate pressure resistant apparatus such as an autoclave of the rotating, rocking or mixing type. After placing the components in the autoclave, it is then sealed following which hydrogen and carbon monoxide are charged thereto until the desired operating pressure has been obtained. Alternatively, as herein-before discussed, as higher pressures are to be employed a portion of the pressure may be afforded by the introduction of a substantially inert gas into the apparatus. After reaching the proper operating pressure, the apparatus is then heated to the desired operating temperature which may range from about 50° to about 300° C. and maintained thereat for a predetermined residence time which may range from about 0.1 hour up to about 10 hours or more in duration. Upon completion of the desired residence time, heating is discontinued and the apparatus and contents thereof are allowed to return to room temperature. Upon reaching room temperature the pressure is discharged, and the apparatus is opened, and the reaction mixture is recovered therefrom.

It is also contemplated that the hydroformylation reaction may be accomplished by utilizing a continuous method of operation. When utilizing this type of operation, the olefinic hydrocarbon is continuously charged to a reaction zone which is maintained at the proper operating conditions of temperature and pressure and which contains a catalyst of the type hereinbefore set forth as well as the nitrogen-containing modifier. Alternatively, the nitrogen-containing modifier may also be continuously charged to the reaction zone either separately or along with the olefinic hydrocarbon charge. In addition to the continuous charging of the reactants to the operating zone, hydrogen and carbon monoxide either separately or in admixture are also charged thereto. Upon completion of the desired residence time in the reaction zone, the reactor effluent is continuously withdrawn and treated in a manner herinafter set forth in greater detail.

The hydroformylation products which are recovered from either the batch type operation or continuous method of operation are then contacted with a nitrogen-containing compound which acts as a solvent for separation and recovery of the metal carbonyl or organometallic catalyst. As hereinbefore set forth, the nitrogen-containing compound which acts as the extractant must be water-soluble and capable of acting as a complexing agent. In addition, the nitrogen-containing compound should also possess other desirable characteristics such as having a boiling point lower than the nitrogen-containing compound which was used as the catalyst modifier while the boiling point of the nitrogen-containing compound which was used to modify the catalyst complex should be less than the boiling point of the hydroformylation products. The contact of the hydroformylation product with the nitrogen-containing compound is effected at reaction conditions which include a temperature in the range of from about ambient to about 100° C. and a gauge pressure in the range of from about 0 to about 1000 pounds per square inch (psig). The contact of the hydroformylation product with the nitrogen-containing compound of the type hereinbefore set forth in greater detail is effected for a period of time which may range from about 0.1 to about 10 hours or more in duration. In addition, in the preferred embodiment of the invention the extraction of the metal from the hydroformylation product is effected in an aqueous medium, thus necessitating the use of a nitrogen-containing compound which is water-soluble in nature. Following the extraction of the metal-containing complex from the organic phase of the solution, the metal free hyroformylation products may be separated by conventional means such as distillation, decantation, etc., while the metal-containing complex in the nitrogen-containing extractant may be then treated in any manner known in the art to recover said catalyst after separation from the extractant, said catalyst being maintained in a solution containing the modifying nitrogen-containing compound.

BRIEF DESCRIPTION OF THE DRAWING

The present invention will be further illustrated with reference to the accompanying drawing which sets forth an illustrative flow diagram of one embodiment of the process of this invention. The flow diagram is operative when the boiling point of the extracting nitrogen-containing compound is less than the boiling point of the nitrogen-containing compound which was utilized to modify the catalyst as well as being passed on the assumption that the boiling point of the latter compound, that is, the modifying nitrogen-containing compound is greater than 100° C. and less than the boiling point of the hydroformylation products. It is to be understood that various valves, pumps, etc., have been eliminated as not being essential to the complete understanding of the present invention. However, the utilization of these as well as other similar appurtenances will become obvious as the drawing is described.

DESCRIPTION OF THE DRAWING

Referring now to the drawing, a charge stock comprising an olefinic hydrocarbon or a mixture of olefins and paraffins is charged to hydroformylation reactor 1 through lines 2 and 3. In addition, a blend gas comprising a 1:1 mole ratio of carbon monoxide and hydrogen is also charged through lines 2 and 3 along with the charge stock to reactor 1. In hydroformylation reactor 1 the charge stock is contacted with a catalyst of the type hereinbefore set forth in greater detail along with nitrgen-containing modifier which is charged through lines 3 and 4 to reactor 1 in a start-up or make-up amount. In reactor 1 which is maintained at hydroformylation reaction conditions which include a temperature in the range of from about 50° to about 300° C. and a pressure in the range of from about 10 to about 300 atmospheres, the olefinic charge stock undergoes hydroformylation to form oxygenated products such as aldehydes or alcohols which contain one carbon atom more than the original charge stock. The products from the hydroformylation including some of the rhodium-containing catalyst are withdrawn from hydroformylation reactor 1 through line 5 and passed to high pressure separator 6. In high pressure separator 6 the gaseous carbon monoxide and hydrogen which have not undergone reaction are separated and recycled to reactor 1 through lines 3 and 7. The bottoms from high pressure separator 6 comprising the hydroformylation products and catalyst are withdrawn through line 8 and passed to extraction column 9. In extraction column 9 the products containing the catalyst are contacted with an aqueous nitrogen-containing solvent which is charged to column 9 through line 10. In extraction column 9 the product containing the catalyst is contacted with the aforementioned extractant material at a temperature in the range of from about ambient to about 100° C. and a pressure in the range of from about 0 to about 1000 psig. The catalyst which is extracted and which will be in the aqueous nitrogen-containing solvent is withdrawn from column 9 through line 11 and passed to distillation column 12. The metal-free hydroformylation products along with the nitrogen-containing compound which modified the catalyst, and which is not soluble in water, are withdrawn from column 9 through line 13 and passed to a second distillation column 14.

In distillation column 14 the hydroformylation product is separated from the modifying nitrogen-containing compound by conventional means. Thereafter the nitrogen-containing compound acts to modify the catalyst, is withdrawn from column 14 through line 15, and recycled to hydroformylation reactor 1 through lines 3 and 15. A portion of this modifying compound is withdrawn from line 15 through line 16 and passed to distillation column 12. In distillation column 12 the catalyst is separated from the aqueous amine solution and in conjunction with the modifying nitrogen-containing compound is recycled to hydroformylation reactor 1 through lines 3 and 17. The aqueous nitrogen-containing extractant is withdrawn from column 12 through line 18 and recycled to extraction column 9 for contact with the hydroformylation product and catalyst.

The hydroformylation product is withdrawn from distillation column 14 through line 19 and passed to a third distillation column 20 wherein the hydroformylation products comprising aldehydes and alcohols are withdrawn through line 21 for recovery while any heavy material or bottoms is removed through line 22.

It is to be understood, of course, that variations and modifications may be made to the illustrative flow scheme without necessarily departing from the scope of this invention. For example, if it is desired to recycle water along with the catalyst, the catalyst recycled will comprise the nitrogen-containing compound, water, and the metal-containing complex, there being a phase separation at the high pressure separator so that the aqueous phase is drawn off and passes immediately to distillation column 12 while the organic phase passes to extraction column 9.

Examples of hydroformylation products which may be prepared by utilizing the present process will include propaldehyde, butyraldehyde, valeraldehyde, caproicaldehyde, heptylaldehyde, caprylicaldehyde, nonylaldehyde, capricaldehyde, laurylaldehyde, propyl alcohol, the isomeric butyl alcohols, pentyl alcohols, hexyl alcohols, heptyl alcohols, octyl alcohols, nonyl alcohols, decyl alcohols, undecyl alcohols, dodecyl alcohols, tridecyl alcohols, tetradecyl alcohols, pentadecyl alcohols, hexadecyl alcohols, heptadecyl alcohols, octadecyl alcohols, nonadecyl alcohols, eicosyl alcohols henicosyl alcohols, docosyl alcohols, tricosyl alcohols, tetracosyl alcohols, pentacosyl alcohols, hexacosyl alcohols, heptacosyl alcohols, octacosyl alcohols, nonacosyl alcohols, triacontyl alcohols, henitriacontyl alcohols, etc.

The following examples are given for purpose of illustrating the process of this invention. However, it is to be understood that these examples are merely illustrative in nature and that the present process is not necessarily limited thereto.

EXAMPLE I

In this example 40 grams of the products resulting from the hydroformylation of 1-octene which comprises a nonanol along with 40 grams of an aqueous ammonium hydroxide solution which contained 29.9 wt. % ammonium hydroxide were placed in a Pyrex bottle fitted with diplegs and valves for sampling, a pressure gauge and a magnetic stirrer. The hydroformylation product contained the catalyst used in said hydroformylation reaction, said catalyst comprising chlorodicarbonylrhodium dimer which had been modified by the presence of N,N'dimethylododecylamine. The bottle was sealed and heated to a temperature of 50° C. for a period of 1.5 hours. At the end of the 1.5 hour period heating was discontinued and after the flask had returned to room temperature the reaction mixture was recovered. The aqueous layer was separated from the organic layer and both layers were analyzed to determine the amount of rhodium extracted from the hydroformylation product. The distribution coefficient, $D_{Rh}$, which is defined as the rhodium in the aqueous phase divided by the rhodium in the organic phase was 39.8, 117.2 wt. % of the rhodium being recovered.

When the above experiment was repeated using similar amounts of extractant, an emulsion formed during the mixing, only 70.7 wt. % of the rhodium being recovered.

The extraction of rhodium from the hydroformylation product was again repeated using 40 grams of an aqueous ammonia solution which contained only 5.1 wt. % of ammonia. As in the previous experiments, this aqueous solvent was admixed with 40 grams of a hydroformylation product comprising nonanol, said product also containing the catalyst used to form the nonanol from 1-octene consisting of chlorodicarbonylrhodium dimer which was modified with N,N-dimethyldodecylamine. The extraction was repeated using conditions identical to those set forth above, the distribution coefficient in this instance being 8.8 with a 130.7 wt. % recovery of the rhodium.

EXAMPLE II

A mixture of 40 grams of an aqueous dimethylamine solution containing 30.0 wt. % dimethylamine and 40 grams of a hydroformylation product resulting from the reaction of 1-octene with carbon monoxide and hydrogen in the presence of a catalyst comprising chlorodicarbonylrhodium dimer which had been modified with N,N-dimethyldodecylamine was treated at a temperature of 50° C. with continuous stirring for a period of 1.5 hours. After separation of the nonanol analysis of the aqueous layer and organic layer disclosed a distribution coefficient of 15.9 with a 93.7 wt. % recovery of rhodium.

EXAMPLE III

The above experiment was repeated using 40 grams of an aqueous solution of N,N-dimethylethanolamine to treat 40 grams of a hydroformylation product containing a catalyst similar in nature to that hereinbefore set forth above. The mixture was treated for a period of 3 hours at a temperature of 50° C. and a pressure of 20 psig of nitrogen. Analysis of the aqueous and organic layers after separation of the nonanol showed a distribution coefficient of rhodium of 9.63 with 135.3 wt. % recovery of rhodium.

EXAMPLE IV

In this example 40 grams of an aqueous solution of pyrrole in which the concentration of pyrrole in the solution was 30.2 wt. % was used to treat 40 grams of a hydroformylation product similar in nature to that set forth in the above examples. The mixture was treated at a temperature of 50° C. with continuous stirring for a period of 2.5 hours. At the end of this time the reaction mixture was recovered and after separation of the nonanol the aqueous layer and organic layer were analyzed. The distribution coefficient of rhodium was found to be 0.30 with a 92.9 wt. % recovery of rhodium.

Similar examples using triethylamine gave a distribution coefficient of rhodium of 0.034 with a 62.7 wt. % recovery of rhodium while the use of ammonium carbonate resulted in a distribution coefficient of rhodium of 0.064 with an 89.0 wt. % recovery of rhodium.

We claim as our invention:

1. A process for the extraction of a Group VIII metal catalyst contained in the products of a hydroformylation reaction of an olefin, carbon monoxide and hydrogen in the presence of said catalyst, the catalyst being in the form of a metal carbonyl or organometallic complex in homogeneous admixture with said reaction products, which process comprises treating the catalyst-containing reaction products, at a temperature of from about ambient to about 100° C. and a pressure of from about 0 to about 1000 psig., with the addition of an aqueous solution of a water-soluble nitrogen-containing compound selected from the group consisting essentially of ammonia, ammonium hydroxide and amines capable of acting as a complexing agent at said temperature and pressure, wherein said added nitrogen-containing compound complexes with said catalyst and recovering a separated aqueous phase containing the extracted resultant metal-containing complex.

2. The process as set forth in claim 1 in which said water soluble nitrogen-containing compound comprises tertiary amine compound.

3. The precess as set forth in claim 2 in which said tertiary amine is an alcohol amine.

4. The process as set forth in claim 3 in which said alcohol amine is N,N-dimethylethanolamine.

5. The process as set forth in claim 1 in which said amine compound is N,N-dimethylamine.

6. The process as set forth in claim 1 in which said metal carbonyl or organometallic complex is synthesized under hydroformylation conditions from catalyst precursors comprising a Group VIII metal, metal salt, metal hydroxide, or metal oxide.

7. The process as set forth in claim 1 in which the metal portion of said metal carbonyl or organometallic complex is rhodium.

8. The process as set forth in claim 1 in which said metal carbonyl or organometallic complex is modified by the presence of an amine.

* * * * *